United States Patent
Tan (10) Patent No.: US 10,058,401 B2
(45) Date of Patent: Aug. 28, 2018

(54) ORTHODONTIC DEVICE

(71) Applicant: Innobrace Orthodontics Pte Ltd, Singapore (SG)

(72) Inventor: Kok Liang Tan, Singapore (SG)

(73) Assignee: INNOBRACE ORTHODONTICS PTE LTD

( * ) Notice: Subject to any disclaimer, the term of this patent is extended or adjusted under 35 U.S.C. 154(b) by 422 days.

(21) Appl. No.: 14/230,478

(22) Filed: Mar. 31, 2014

(65) Prior Publication Data
US 2015/0272706 A1    Oct. 1, 2015

(51) Int. Cl.
| | | |
|---|---|---|
| *A61C 3/00* | (2006.01) | |
| *A61C 7/14* | (2006.01) | |
| *A61C 7/12* | (2006.01) | |
| *A61C 7/28* | (2006.01) | |

(52) U.S. Cl.
CPC ........... *A61C 7/141* (2013.01); *A61C 7/12* (2013.01); *A61C 7/28* (2013.01)

(58) Field of Classification Search
CPC ............. A61C 7/141; A61C 7/28; A61C 7/12
USPC ........................................ 433/8–24
See application file for complete search history.

(56) References Cited

U.S. PATENT DOCUMENTS

| | | | | |
|---|---|---|---|---|
| 3,327,393 A | * | 6/1967 | Brader | A61C 7/12 433/11 |
| 5,174,754 A | * | 12/1992 | Meritt | A61C 7/12 433/10 |
| 5,356,289 A | * | 10/1994 | Watanabe | A61C 7/30 433/10 |
| 2005/0003320 A1 | * | 1/2005 | Freeman, Jr. | A61C 7/16 433/9 |
| 2007/0134612 A1 | * | 6/2007 | Contencin | A61C 7/12 433/24 |
| 2007/0207436 A1 | * | 9/2007 | Tan | A61C 7/14 433/10 |

* cited by examiner

*Primary Examiner* — Matthew Nelson
(74) *Attorney, Agent, or Firm* — Ladas & Parry LLP; Malcolm J. MacDonald (57) ABSTRACT

An orthodontic bracket for the re-positioning of a tooth, such that separate walls forming the archwire slot are designed to enable different extents of flexing and movement.

20 Claims, 11 Drawing Sheets

ORTHODONTIC DEVICE

FIELD OF THE INVENTION

The present invention is in respect of an orthodontic device. The invention set out below relates to the design and application of orthodontic brackets and/or buccal tubes for the receipt of archwires to adjust or re-arrange the position of teeth.

BACKGROUND OF THE INVENTION

Orthodontics is a branch of dentistry that re-aligns ill-positioned teeth to enable full and proper functioning of the teeth as well as improve the appearance.

There are several treatment options that may be prescribed including the use of aligners and orthodontic brackets.

The treatment option involves orthodontic brackets that are fixed and bonded to the surfaces of a continuous row of teeth. Specifically, the brackets are bonded on the inside (lingual) surfaces or outside (labial or buccal) teeth surfaces.

The current design of orthodontic brackets may be separated into three categories i.e. conventional brackets with ligatures, self-ligating brackets and non-ligating brackets.

The conventional bracket with ligature has a rectangular slot to receive the orthodontic archwire that provides the tensile forces to re-align teeth. This archwire is inserted along the longer sides of the rectangular slot of each bracket and continues through the rectangular slots of all the other brackets along the same row of brackets on the same side of the teeth or in the same arc. The archwire is either rectangular or round in cross-section. The archwire ends on either end at or behind the last tooth that has a bracket in the same arc.

The two narrower or shorter sides of each rectangular slot of a bracket are vertical or almost vertical (relative to the upright person) and the two longer sides of the rectangular slot are horizontal or almost horizontal (relative to the upright person) when the bracket has been bonded on the tooth, and perpendicular or almost perpendicular with the enamel surface of the tooth on which the bracket is fixed. The two longer sides of the rectangular slot are also referred to as the occlusal wall (that nearest the biting surface or edge of the tooth) and gingival wall (that nearest the gum margin).

One of the narrower side of the rectangular slot would usually be open for the purpose of receiving the continuous archwire. For brackets bonded on the inside surfaces of teeth, the opening of each slot for this purpose of receiving the archwire is usually on the lingual or occlusal side. For brackets bonded on the outside surfaces of teeth, the opening of each slot is on the labial or buccal side. This is the case for the three kinds of brackets: ligating, self-ligating and non-ligating.

The current technology relies on the tension in the archwire to create a force on each tooth to re-position the tooth over time. From time to time, the wire needs to be changed or readjusted to renew the tension in the wire as the force decays over time, or to adjust the direction of the force as the tooth gradually shifts.

In orthodontics, the ideal type of force to be exerted on a tooth is a gradual or gentle but continuous force, as opposed to a strong but intermittent force or a force that decreases in strength over time. A typical force exerted on each tooth (for the purpose of re-alignment) is 200 grams or less. Excessive force causes pain and may retard the movement of the tooth.

The types of available brackets primarily focus on the securing of the archwire but are otherwise a passive receptacle in the orthodontic process. It is the use and positioning of the archwire that creates the necessary and differing forces overtime for the re-positioning of the tooth.

It is a common practice for an orthodontist to use a round archwire at the start of the treatment, and then progress to a thicker archwire that may be round or rectangular in cross-section. The reason for this is that a thicker archwire enables a greater scope for three-dimensional control over the strength and direction of the force to be created over the tooth. The rectangular nature of the archwire improves this three-dimensional control and the force that can be created.

This need to have graduated forces over time arises from consideration of speed of correction. The initial fitting of the brackets and archwire tends to create pain to the patient and some trauma to the teeth because it is anticipated that the archwire would decrease in tension overtime and to accommodate this, the archwire is usually adjusted to take this in account. If, to totally eliminate pain, the archwire was insufficiently taut, the orthodontic effect would be greatly reduced and natural decaying of the force would mean slower progress in the treatment and a greater number of visits to the orthodontist.

These several limitations arise from the primary reliance on the wire to create the necessary corrective orthodontic treatment is because the bracket is designed as a passive holder of the archwire.

Ligating Brackets

The application of orthodontic forces depends on the archwire continuing to reside in the archwire wire slots. For ligating brackets, this is achieved with the use of ligatures to tie the archwire to the brackets.

A common type of orthodontic ligature is a small elastomeric ring that is made from polyurethane that is stretched around tiewings. The latter are legs (protrusions) fixed to the gingival and occlusal aspects of the body of the bracket. Once employed, the elastomeric ring extends around the tiewings and the labial aspect of the archwire and when suitably adjusted, the ring applies a seating or downward orthodontic force on the archwire in the direction of the archwire slot.

A degree of movement should be allowed for the archwire within the archwire slot for optimal tooth movement. This desired degree of movement in turn depends on the unchanging space within the rigid walls of the archwire slot and the adjustment of the ligature that in turn alters the available space within the walls as well as the degree of the downward pressure exerted by the ligatures to seat the archwire. This may create difficulty because the degree of flexibility is not easily attained with ligatures that exert a one-directional non-changing force on the archwire. The rigid walls of the archwire slot do not flex to interact with the ligature to produce a varying and/or re-directed force on each tooth to either absorb the excessive force or to produce a more effective force for re-aligning the tooth.

Another disadvantage of the elastomeric ring (as a ligature) is the tendency of the material to decay and stain and resulting in depreciation of the force required for the tooth alignment. The ring also allows the build-up of bacterial plaque and may sometimes dislodge or disengage from the bracket. A newly-installed elastomeric ring may cause a gripping force on the archwire that in turn pushes against the bracket with the likely consequence of unnecessary friction between the archwire and the bracket. This is undesirable as it does not promote optimum tooth movement.

The alternative to the elastomeric ring is the metal ligature made of stainless steel. It is applied in similar fashion to secure and retain the archwire in the archwire slots of brackets. Save that there is no decay or staining for metal ligatures, the same disadvantages for the elastomeric ring are applicable here as well. There is a risk that the metal ligature may come loose in the mouth from contact with food or brushing and affect the inside of the mouth. Additionally, metal ligatures take a longer time to fit because the ends of the metal ligature are twisted and secured over the tiewings of the brackets, although there is more control over the extent of tightness and degree of grip that varies to an extent on the degree of twisting and securing of the metal ligature ends (unlike for elastomeric rings).

In summary, the ligature system is time consuming to implement and there is risk of dislodgement or disengagement of the ligature. The additional implement of pliers is required to install and shift the ligature on the bracket tiewings.

Self-ligating Brackets

Self-ligating brackets seek to overcome some of the above problems and challenges.

These brackets dispense with the use of ligatures and rely on an attached moveable component of the bracket to open and securely close the archwire slot that receives the archwire. This moveable component ordinarily is made up of a clip or hook or cover or any component that can close the slot securing the archwire and restricting its movement.

Self-ligating orthodontic brackets that are disclosed in the following documents:

a) U.S. Pat. Nos. 5,094,614, 5,322,435, 5,613,850 and 8,414,292, disclosing sliding closure latches;

b) U.S. Pat. Nos. 3,772,787, 4,248,588 and 4,492,573, disclosing U-shaped ligating latch clips;

c) U.S. Pat. Nos. 4,103,423, 4,371,337, 4,559,012, 4,712,999 7,878,802 and 7,963,767, disclosing cover-plate type latches using rotatable locking mechanisms;

d) U.S. Pat. Nos. 5,516,284, 5,685,711, 5,711,666 and 7,621,743, disclosing cover-plate type latches using spring mechanisms;

e) U.S. Pat. No. 7,677,887, disclosing a shape memory self-ligating orthodontic bracket which has archwire retainers formed of shape memory materials;

f) U.S. Pat. No. 6,582,226 B2 discloses an orthodontic device with a self-releasing latch.

While self-ligating brackets dispense with the drawbacks of ligatures (as above-described), they have their own disadvantages. The common feature of all self-ligating orthodontic brackets is at least one moveable component that can be adjusted to either to open the archwire slot (to enable receiving or removing or adjustment of the archwire) and to close the slot to secure it. The open and closed positions can be achieved by the movement of the component or components.

To attain some measure of security in the closed position, implements are required to both close and open the slot. This is an additional step and is time consuming due to various factors such as the smallness of the moveable component or components, and the delicate nature of such components. The variety of such locking and opening devices in different types of self-ligating brackets also mean that the orthodontist needs to be skilled in the different methods of opening and closing the brackets. Where excessive force is used in the closure or opening of the brackets, there may be fatigue, distortion or damage to the bracket that may affect its effectiveness in holding down the archwire and further adversely affect the corrective force of the archwire. Different implements have to be employed for different types of self-ligating brackets due to their different securing and release mechanisms. There is also the risk of disengagement or breakage of the moveable component or components from the body of the bracket that may be due to stress, improper release, brushing or contact with food or drink. This poses a risk of swallowing or injury to the mouth.

Non-ligating Brackets

The third type of orthodontic bracket disclosed in the art is the non-ligating bracket (Great Britain Patent GB 2423937) (Application No 0609139.1). This is the application filed by the same applicant for this current application.

This third type of orthodontic bracket is a single piece device with no moveable parts such as those in the non-ligating brackets above-described and not requiring any ligature such as those in the traditional brackets above-described. It is made as a solid bracket save for a cross-sectional passage cavity within that is shaped to receive and secure the archwire within the passage cavity without the need for ligature or any separate locking or securing components. It has a base that shaped to enable it to be bonded to tooth surfaces and also a narrowed opening at the top of the bracket through which the archwire is received into the passage cavity. The narrowed opening is created as a lobe, extension or protrusion or such like with the purpose that it is more difficult for the archwire inserted through the opening in the ordinary course of usage to be dislodged or loosened from the bracket without the intervention of the orthodontist applying sufficient force to remove the archwire from the bracket.

The absence of tiny moveable parts or components means there is no risk of detachment of such moveable parts or components. There is also no need to use instruments to open and close the brackets through the manipulation of the moveable parts or components, as is necessary for the self-ligating brackets. The construction of this third type of orthodontic bracket is also simpler as it is constructed as one piece.

However, the drawbacks to this third type of bracket are that the bracket, being constructed as single-piece solid bracket, does not provide for the desired flexibility of its occlusal and gingival walls. This disadvantage is true of all other orthodontic brackets including the traditional brackets and non-ligating brackets and self-releasing brackets. The advantage of insertion of the archwire into the third type of orthodontic bracket without the use of implements is more than counteracted by the relatively stronger pressure required to push the archwire past the narrowed opening. The same applies to the removal or adjustment of the archwire. For a bracket of such small dimensions, such stronger pressure imposes undue stress on the bracket causing micro-fractures that may result in breakage or reduced effectiveness in the corrective forces from the archwires. Durability of such brackets is drastically reduced, resulting in the needed to replace the bracket or brackets during treatment, which entails further time and cost. The usual practice of replacing progressively thicker and stiffer archwires throughout the treatment means that stresses caused by the replacement increase. There is also undue pain and discomfort from having to insert the increasingly thicker wires through the same narrow opening of the bracket. The inflexibility of the walls also do not provide shock absorbency and the torque and tip forces from the archwire are not dissipated evenly and gently to the tooth. Due to the rigidity of the bracket walls, there is less scope to create differentiated forces through manipulating the archwire in the third type of bracket. As earlier described, all the brackets (ligating, self-ligating and non-ligating) are designed as rigid structures to merely hold in place the archwire in the archwire slot. The bracket does not perform any function relating to the differentiation or graduation of forces or any function relating to the exertion of forces. It does not perform any shock absorbency function either.

Any discussion of documents, devices, acts or knowledge in this specification is included to explain the context of the invention. It should not be taken as an admission that any of the material forms part of the art or the common general knowledge in the relevant art anywhere in the world on before the priority date of the disclosure and claims herein.

The present invention is to provide a more effective orthodontic bracket, greater ease of implementation as well as alleviate or provide a solution to at least one disadvantage associated with the existing art.

BRIEF DESCRIPTION OF THE DRAWINGS

Further disclosure, objects, advantages and aspects of the present application may be better understood by those skilled in the relevant art by reference to the following description of the preferred embodiments taken in conjunction with the accompanying drawings, which are given by way of illustration only, and thus are not limitative of the present invention, and in which.

DETAILED DESCRIPTION OF THE INVENTION

According to the present invention, the orthodontic device (25) and systems and methods are provided for incrementally moving teeth by the use of an orthodontic bracket (affixed to a tooth) that receives in its slot an archwire and with specially designed hollow walls that flex upon being pushed by the archwire that is variously positioned to create different types of forces to correct the alignment of the tooth (26).

Figure 1:
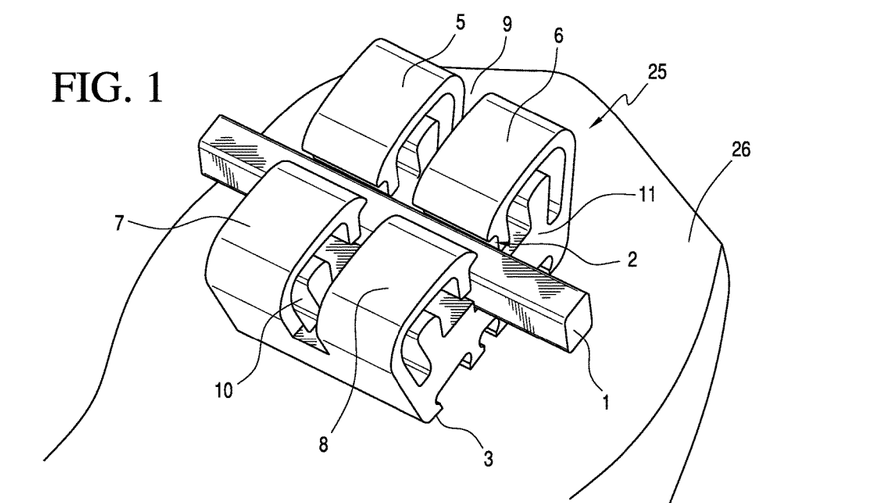
FIG. 1 illustrates a three-dimensional view of the orthodontic device of the present invention standing on its base, and showing the positioning of the archwire.
Figure 2:
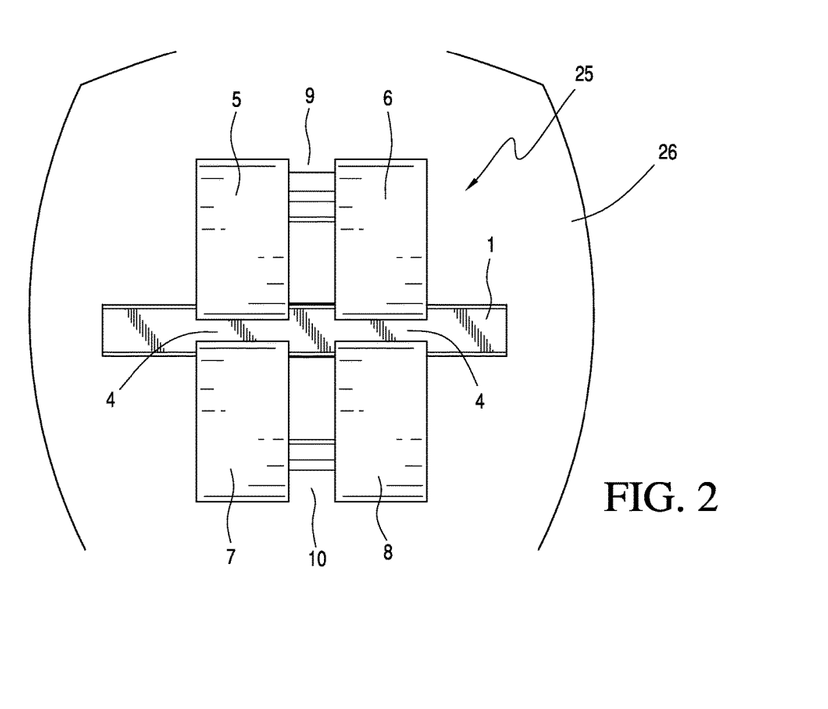
FIG. 2 illustrates a plan view of the orthodontic device of FIG. 1.

Referring now to FIG. 1 and FIG. 2, one embodiment of the present invention is shown respectively in the three-dimensional and plan views. These figures show the way in which the archwire (1) is positioned in the slot (2) of the orthodontic device or bracket (25). The base (3) of one bracket is secured to one tooth (26) in a conventional manner known in the art. The archwire is inserted through the opening (4) of and into the slot. The same archwire is positioned through the slots of a series of the orthodontic devices, each such bracket affixed to the surface of a tooth for the purpose of exerting corrective forces on the teeth. The archwire may be round or four-sided in cross-section, depending on the stage of treatment and/or the type and extent of the corrective force sought to be imposed on the tooth.

Re-adjustment or replacement of the archwire is required over the period of the orthodontic treatment. It is common practice with the current brackets available in the market to start with the round archwire and during the treatment have it replaced by the four-sided archwire as the latter can better exert a stronger force.

Re-adjustment or replacement could be due to several factors including decaying of the corrective force due to the reduction of tension in the archwire, and/or the need to adjust the angle or strength of the corrective force during the progress of the treatment as the tooth is gradually realigned.

The present embodiment is created as a single piece without any separate components attached thereto.

The optimum treatment for re-positioning of teeth is to articulate a continuous force that retains its strength for as long as possible without being excessive as this can cause pain and trauma and impede the corrective treatment. The force also has to be precisely directed for the optimum and most effective correction, which in turn means a shorter treatment time.

Figure 3:
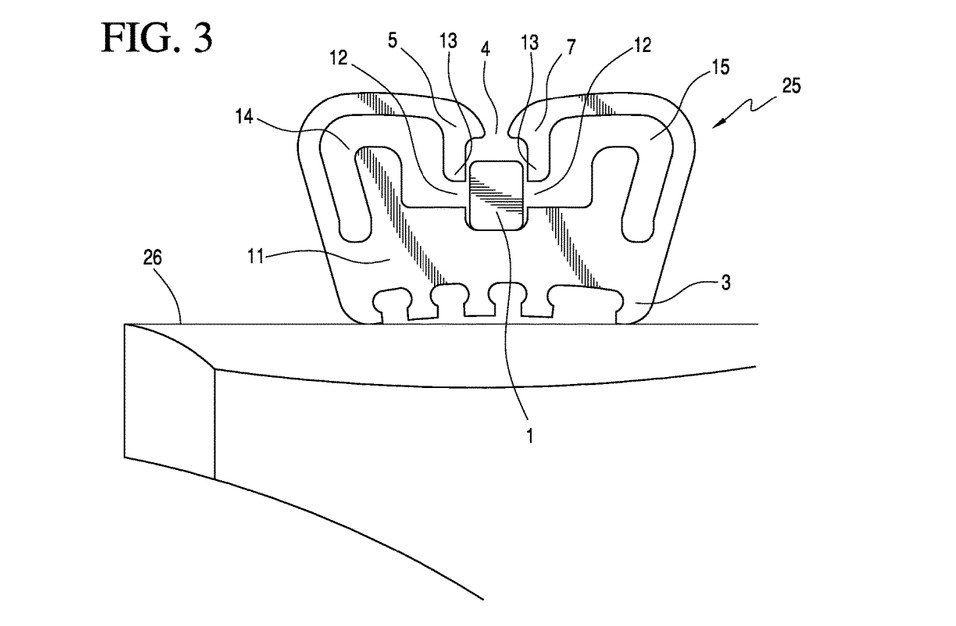
FIG. 3 illustrates a front elevation view of the orthodontic device of FIG. 1.

Referring now to FIG. 1, FIG. 2 and FIG. 3, the archwire slot is shaped by the occlusal walls (5), (6) and gingival walls (7) (8). In the present embodiment of the invention, there are two sets of occlusal walls (5), (6) separated by a gap (9) and two sets of gingival walls (7), (8) separated by a gap (10).

The front elevation view in FIG. 3 shows the hollow space (14) formed by one of the occlusal walls and the other hollow space (15) formed by one of the gingival walls. It also shows a space between (12) the middle segment (11) and the end of the wall (13).

Figure 4:
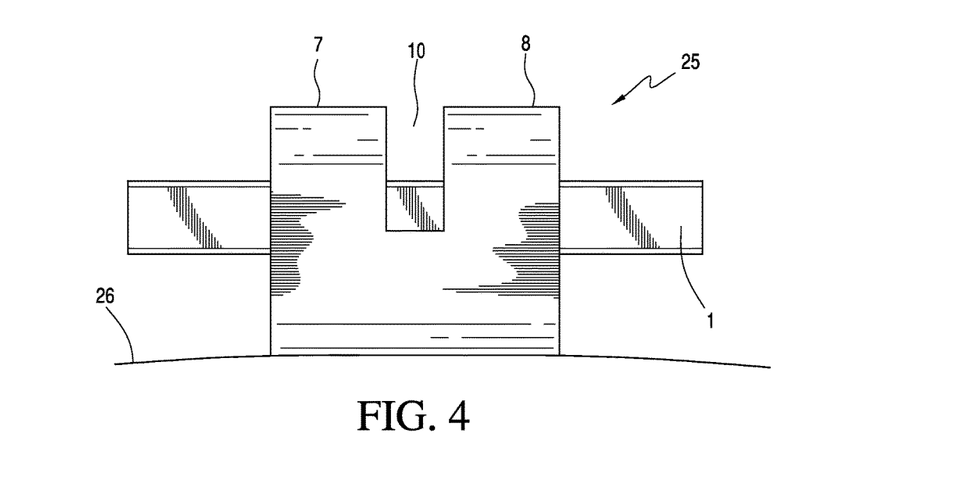
FIG. 4. illustrates a right side elevation view of the orthodontic device of FIG. 1.
Figure 5:
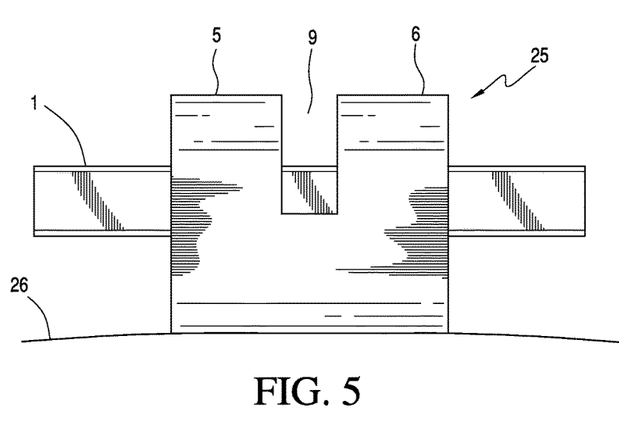
FIG. 5. illustrates a left side elevation view of the orthodontic device of FIG. 1.

FIG. 4 and FIG. 5 show the respective right side and left side elevations of the orthodontic device (25). FIG. 4 shows the gap (10) between the two sets of gingival walls (7), (8). FIG. 5 shows the gap (9) between the two sets of occlusal walls (5) (6).

In the present embodiment of the invention, the thickness of the walls, the hollows (14), (15) formed by the walls, the gaps (12) between the ends (13) of each of the walls and the middle segment (11), and the gap (9) between the occlusal walls (5), (6) and the gap (10) between the gingival walls (7), (8).

These features give the flexibility that is important for the corrective forces of the invention.

In the present embodiment of the invention, there are two sets of occlusal walls and two sets of gingival walls. To cater to different degrees of flexibility, there may be three or more sets of occlusal or gingival walls. The width of the gap (9) between the occlusal walls (5), (6), and the gap (10) between the gingival walls (7), (8), as well as the width of the gap (12) between the end of each wall (13) and the middle segment (11) and the thickness of the respective walls may be varied to introduce different extents of the flexing of the walls that in turn affect the nature and strength of the corrective forces on the teeth. The flexibility is also determined to an extent by the material used for the orthodontic device (25).

One advantage in the flexing of the walls means the increased ease and speed in the fitting of the archwire in the orthodontic treatment process. Together with the design of the walls, the flexibility means the exertion of a lesser force to insert the archwire and hence minimum or no discomfort or pain to the patient. Another advantage is that the impact of a greater force to insert the archwire into the slots of a series of brackets is absorbed by the flexing of the walls to receive the archwire into the respective slot. This prevents trauma to the teeth. Presently, there is no known bracket design with such walls.

Orthodontic treatment requires periodic adjustment of the archwire and this often necessitates the removal of the archwire and/or replacement with a different archwire. The removal process is similarly facilitated by the flexibility of the walls. The ease of removal is enhanced due to shock absorbency of the flexing walls Another advantage is that the use of a suitable material for the bracket and the design of the walls to allow flexibility, as well as the ease of insertion and removal, means less stress to bracket. This flexibility also reduces impact on the brackets arising from eating and brushing during the period they are fitted on the teeth. This in turn reduces the possibility of micro-fractures that weaken and eventually lead to breakage of the bracket, unlike the existing types of brackets that do not have this characteristic. Being constructed without separate appendages, unlike ligating and self-ligating brackets (described under Background of the Invention), there are no drawbacks or disadvantages associated therewith including build-up of bacterial plaque around the elastomeric ring of ligating brackets and the dislodgement or disengagement of separate components from the self-ligating bracket.

Figure 6:
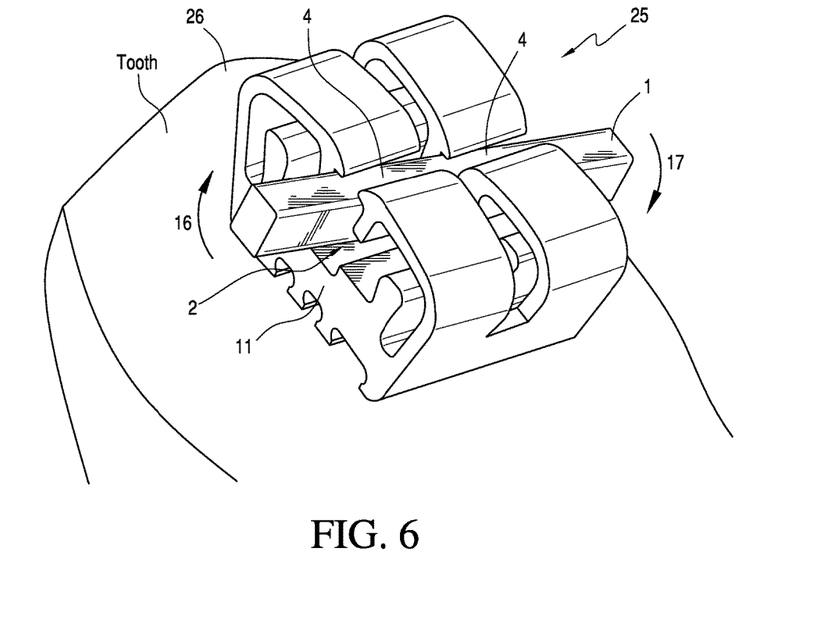
FIG. 6. illustrates a three-dimensional view of the orthodontic device and shows the way in which the archwire is positioned and the flexing of the walls of the orthodontic device to create a rotational effect on the tooth to which the base of the device is attached.

FIG. 6 illustrates the enhancement of the corrective rotational forces arising from the design of the orthodontic device (25).

FIG. 6 shows a three-dimensional view of how the archwire is positioned within the slot (2) of a bracket to create a rotational force. For the person standing upright, this force rotates a tooth on a vertical rotational axis plane to align such tooth in line with other teeth in the same row of teeth so that the teeth are evenly positioned.

FIG. 6 shows the archwire placed at the front elevation at a higher plane (further away from the middle segment (11) of the orthodontic device (25) and nearer the opening (4) of the slot) and at the rear elevation at a lower plane (further away from the opening (4) of the slot and nearer the middle segment (11) of the orthodontic device (25)). The section of the archwire at the higher plane creates a force away from the tooth (26), in the direction indicated by the arrow (16), while the section of the archwire at the lower plane creates a force towards the tooth, in the direction indicated by the other arrow (17). The rotational effect is thus created.

Figure 6A:
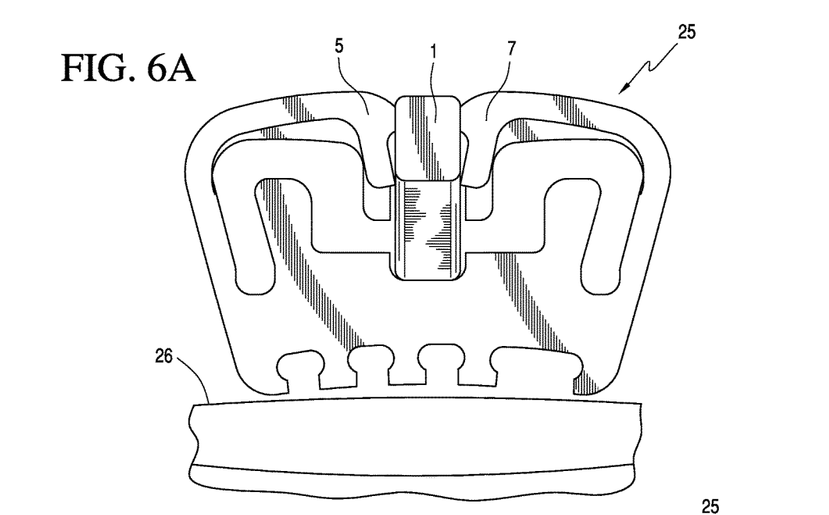
FIG. 6A illustrates a front elevation view of the orthodontic device of FIG. 6 showing the flexing of the walls of the orthodontic device.

FIG. 6A shows the front elevation view of the orthodontic device (25) of FIG. 6 and illustrates the position of the archwire (1) nearer the opening of the slot and the flexing of the occlusal wall (5) and gingival wall (7) from the front elevation due to the interaction of the archwire with such walls.

Figure 6B:
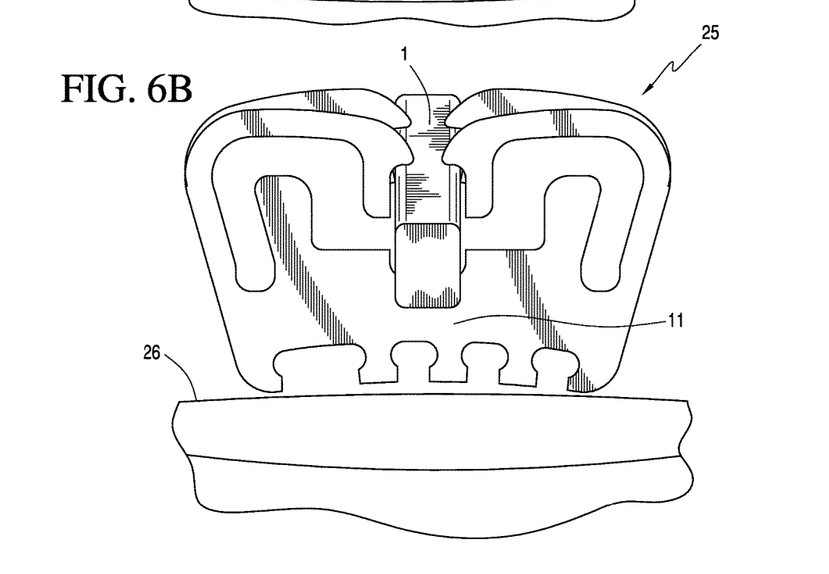
FIG. 6B illustrates a rear elevation view of the orthodontic device of FIG. 6 showing the flexing of the walls of the orthodontic device.

FIG. 6B shows the rear elevation view of the orthodontic device (25) of FIG. 6 and illustrates the position of the archwire nearer the middle segment (11) of the orthodontic device (25).

Figure 6C:
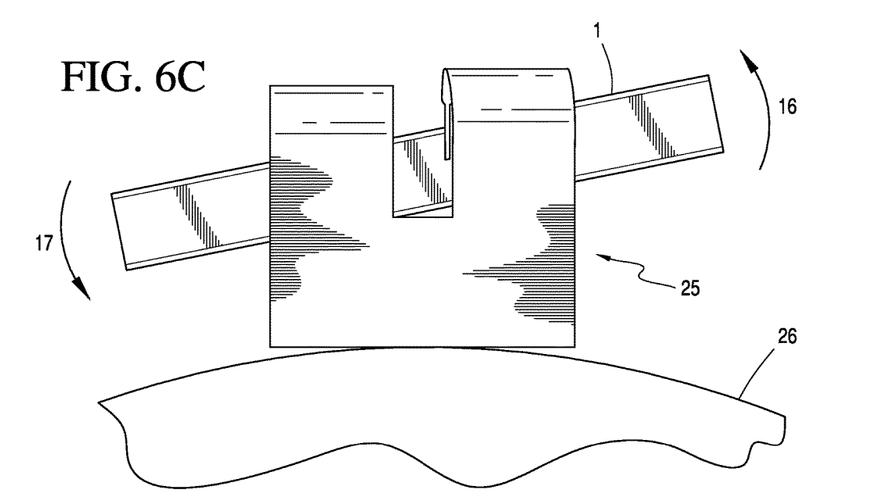
FIG. 6C illustrates a left side elevation view of the orthodontic device of FIG. 6.

FIG. 6C shows the left side elevation view of FIG. 6 and shows the respective direction of the corrective forces (16, 17).

The flexing of the occlusal and gingival walls from the front elevation (FIG. 6A) results in a more continuous and graduated corrective force over a longer period of time. The force exerted by the archwire away from the tooth (26) in the direction indicated by the arrow (16) in FIG. 6 is moderated by the flexing of the walls so as to prevent excessive force that may cause trauma to the teeth. In FIG. 6, the walls (comprising one occlusal wall and one gingival wall) will each exert the same counter-force on the archwire and this helps to maintain a tension in the archwire over a longer period of time, slowing down any decay in the corrective force.

To achieve a corrective force in a varied angle, the archwire may be positioned either more towards any one or more of the four walls (i.e. the two occlusal walls and the two gingival walls). This will result in a moderating effect from the flexing of one or more walls, and also result in any one wall exerting a greater counter-force than another wall. The interaction of the wall or walls being flexed with the archwire creates a more durable and continuous and more precisely angled force than can otherwise be created in existing brackets. The reason for this difference is that existing brackets presently used in orthodontics are primarily designed as passive and non-moving brackets whose purpose is to serve as receptacle for the archwire.

Figure 7:
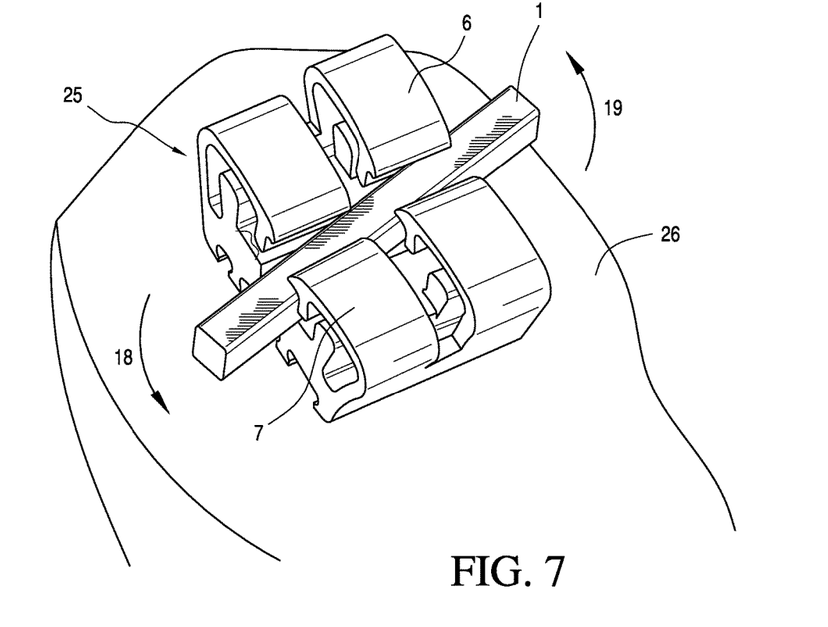
FIG. 7 illustrates a three-dimensional view of the orthodontic device and shows the way in which the archwire is positioned and the flexing of the walls of the device to create a tilting force on the tooth to which the base of the device is attached.
Figure 7A:
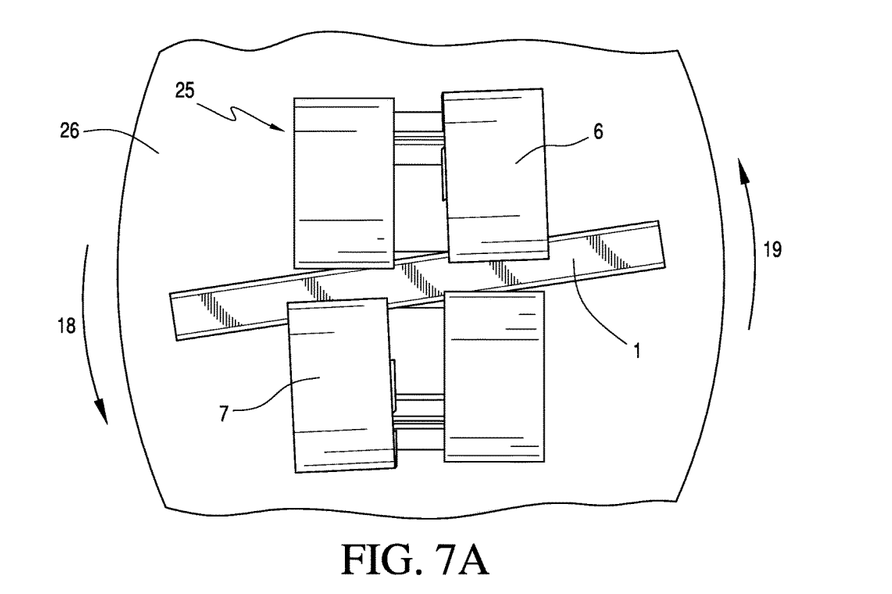
FIG. 7A illustrates a plan view of the orthodontic device and shows the way in which the archwire is positioned and the flexing of the walls of the orthodontic device to create a tilting force on the tooth to which the base of the orthodontic device is attached.
Figure 7B:
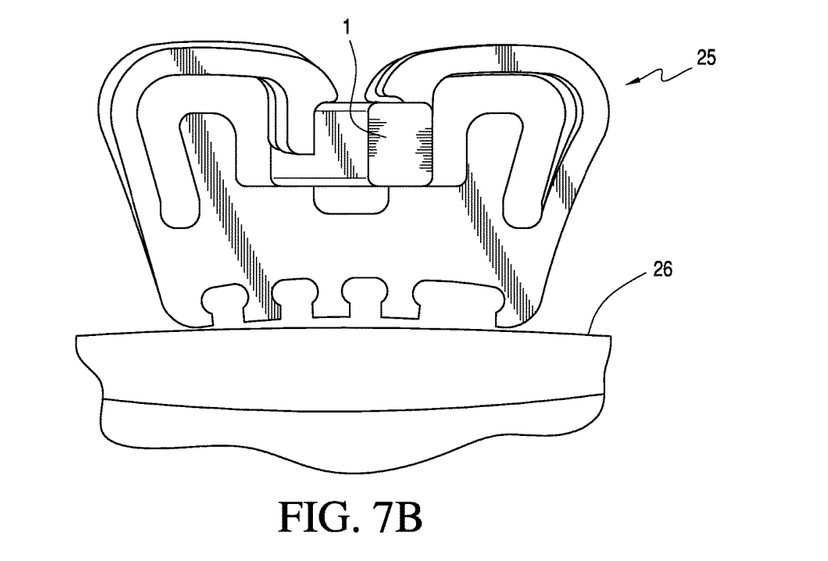
FIG. 7B illustrates a front elevation view of the orthodontic device of FIG. 7 showing the flexing of the walls of the orthodontic device.
Figure 7C:
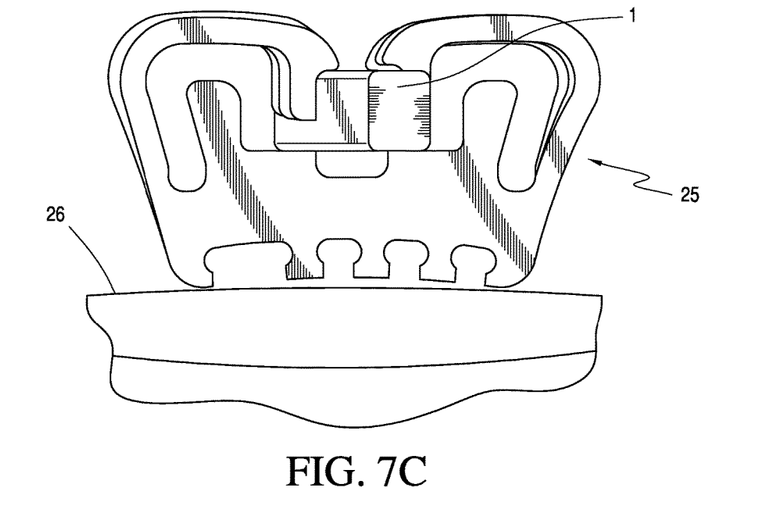
FIG. 7C illustrates a rear elevation view of the orthodontic device of FIG. 7 showing the flexing of the walls of the orthodontic device.

A similar effect is shown in FIG. 7 and FIG. 7A illustrating a different positioning of the archwire that results in the flexing of the walls to create a tilting force on the tooth (26). The archwire is positioned to create a sideway tilt along the vertical plane of the tooth (26) (relative to the upright person), as indicated by the arrows (18), (19).

The illustrations show the positioning of the archwire closer to the gingival wall (7) creates a tilting force on the tooth (26) in the direction indicated by the arrow (18).

The positioning of the archwire closer to the occlusal wall (6) creates a tilting force on the tooth (26) in the direction indicated by the arrow (19).

Again, the interaction of the walls with the archwire creates a more moderated and continuous force not possible under existing orthodontic brackets currently in use.

Where the archwire (with a rectangular cross-section) is turned at an angle within the slot of the orthodontic bracket, it creates yet another force, a torque that moves the tooth (26) inwards or outwards to align it with the vertical plane. Again, the archwire may be turned to push against the flexed wall that in turn pushes back with the effect of absorbing any excessive force and maintaining a continuous lower force.

Figure 8:
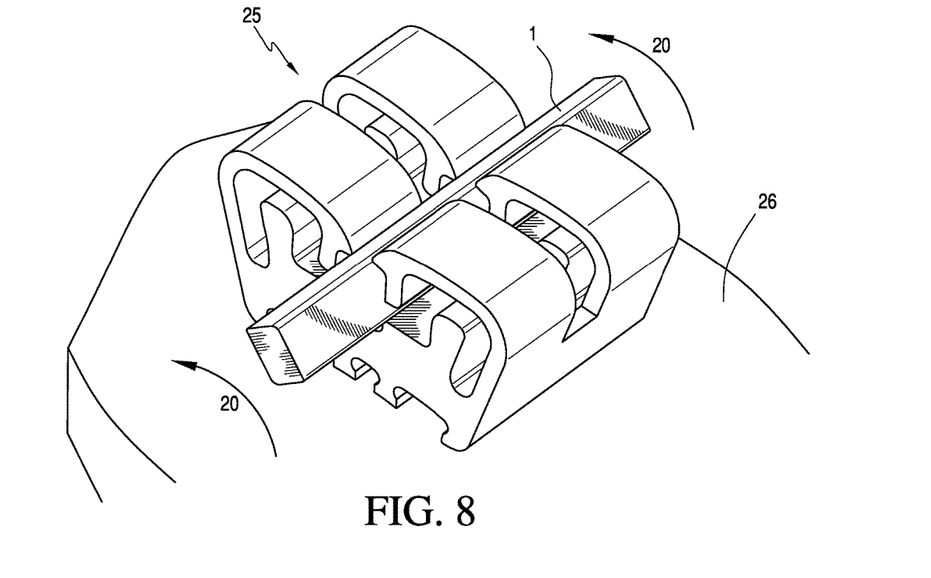
FIG. 8 illustrates a three-dimensional view of the orthodontic device and shows the way in which the archwire is positioned and the flexing of the walls of the orthodontic device to create a torque force on the tooth to which the base of the orthodontic device is attached.
Figure 8A:
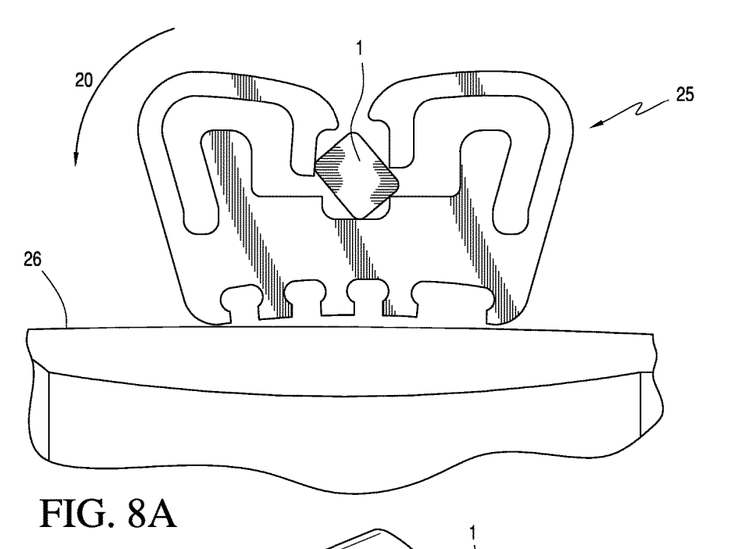
FIG. 8A illustrates a front elevation view of the orthodontic device of FIG. 8 showing the flexing of the walls of the orthodontic device.

FIG. 8 and FIG. 8A show how the turning of the wire creates the torque force in the direction created by the arrows (20).

In addition to the above instances of the archwire positioning, the archwire may be positioned in any other manner to combine any of the torque, tilt and rotational forces. The efficacy of these specifically angled forces is increased with a greater number of occlusal or gingival walls (for instance, a series of three separate occlusal walls). Different extents of the flexing of the walls (due to the use of different materials for separate walls) also allow a sophisticated graduation of angled force along the archwire.

Figure 9:
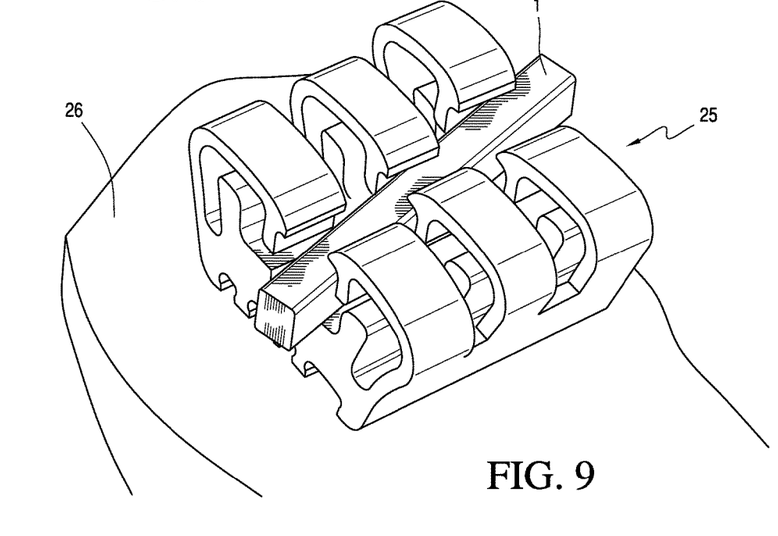
FIG. 9 illustrates a three-dimensional view of a different embodiment of the invention, showing three separate occlusal walls and three separate gingival walls and further showing the different degrees of flexing of the walls.
Figure 9A:
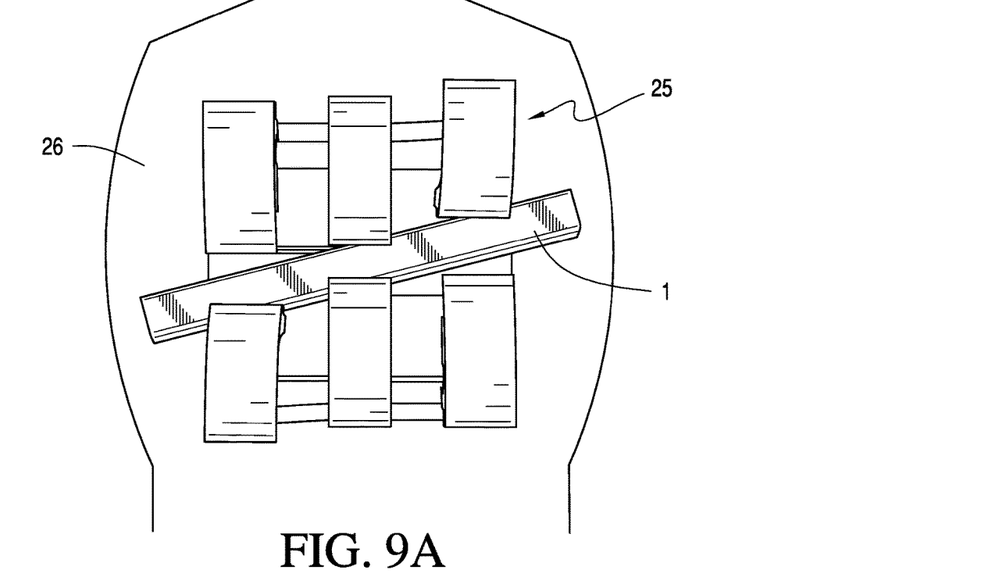
FIG. 9A illustrates a plan view of the orthodontic device in FIG. 9 showing the different degrees of flexing of the walls.
Figure 9B:
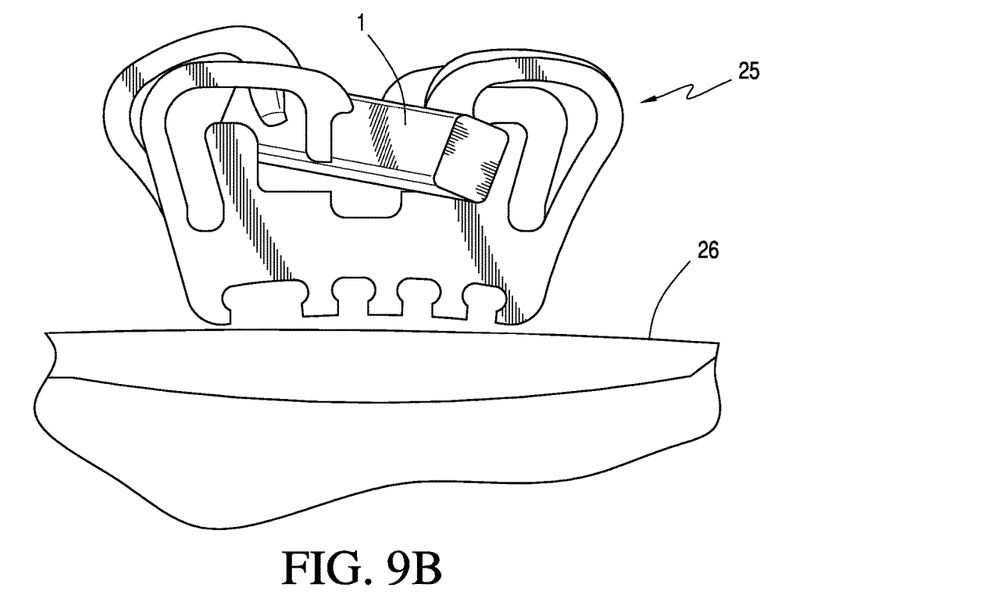
FIG. 9B illustrates a front elevation view of the orthodontic device in FIG. 9.
Figure 9C:
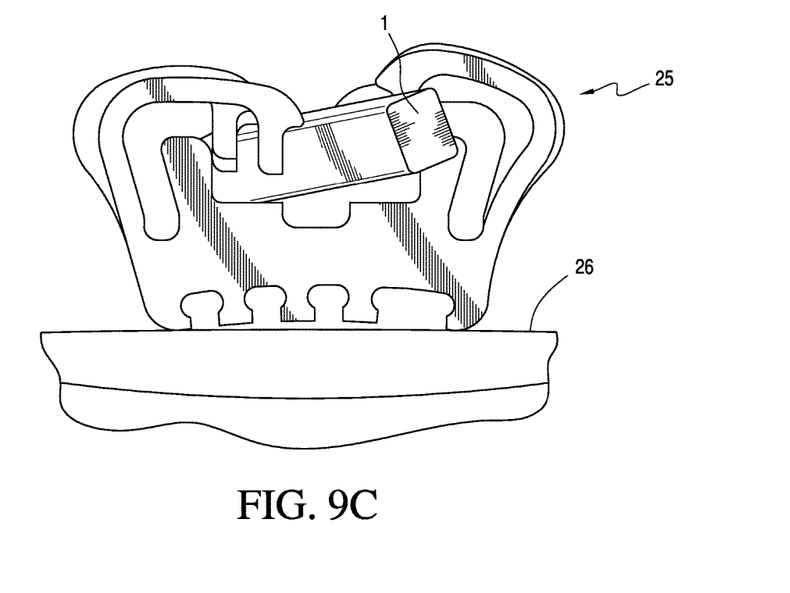
FIG. 9C illustrates a rear elevation view of the orthodontic device in FIG. 9.

FIG. 9 illustrates an embodiment showing six walls and the different extents of the flexing in all the six separate walls (i.e. three occlusal walls and three gingival walls), the varying degrees of flexing indicated by the length of the respective arrows). FIGS. 9A, 9B and 9C respectively show the plan, front elevation and rear elevation views of the embodiment in FIG. 9.

Due to the interactive push and corresponding reaction between the wall and the archwire, different tensions may be created along the section of the archwire within the same bracket. This results in forces of varying strengths, enabling precise corrective treatment in the form of precisely angled forces and/or increasing duration of the corrective forces.

Overall, the results of the corrective treatment are more satisfactory due to greater accuracy in re-positioning while the corrective treatment period is abridged, saving time, costs and the reduction of any cumulative pain or discomfort.

The above characteristics and effects of the above orthodontic device enable the orthodontist to increase the tension in the archwire to provide a greater force without traumatizing the teeth. This may be implemented even at the start of the orthodontic treatment. This is in contrast to the present procedure (using currently available brackets) that at the start of the treatment usually creates a lesser force to reduce pain and discomfort.

The drawback to creating a lesser force by reducing the tension in the archwire means that more regular follow-up treatments are required to renew the corrective forces through the adjustment of the existing archwire or the replacement of the existing archwire with a thicker wire to create a strong force. Overall, this will involve a greater amount of treatment time and costs.

A possible treatment option for current orthodontic brackets is to increase the force by increasing the tension in the archwire. This, however, has the undesired effect of causing great discomfort and pain.

Figure 10:
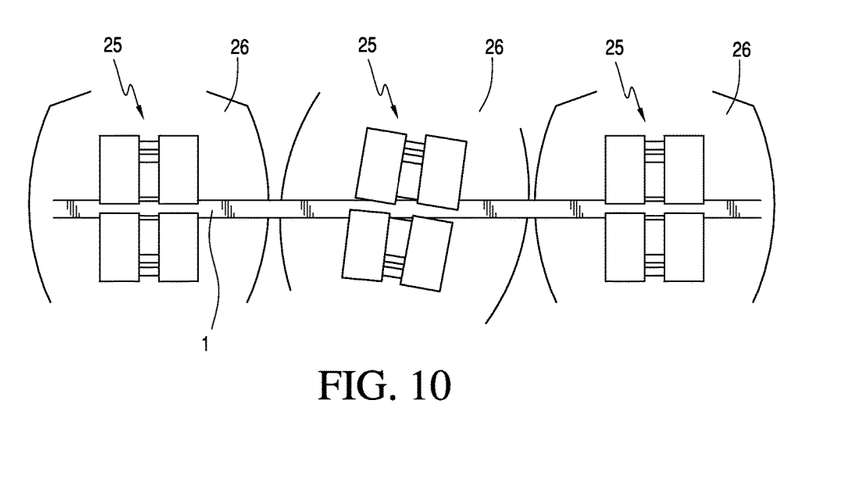
FIG. 10 illustrates a plan view of a series of three orthodontic devices, each on a tooth, illustrating the manner of the extent of the flexing of the walls of the devices to accommodate the uneven nature of the teeth

The extent to which the archwire (1) may be twisted or angled from tooth to tooth as it is slotted through a series of orthodontic devices, is illustrated in FIG. 10. The more uneven the teeth, the greater the archwire must be twisted or angled from tooth to tooth. This shows that the greater the twisting of the archwire, the greater the force exerted on the teeth and at the base of the device.

Figure 11:
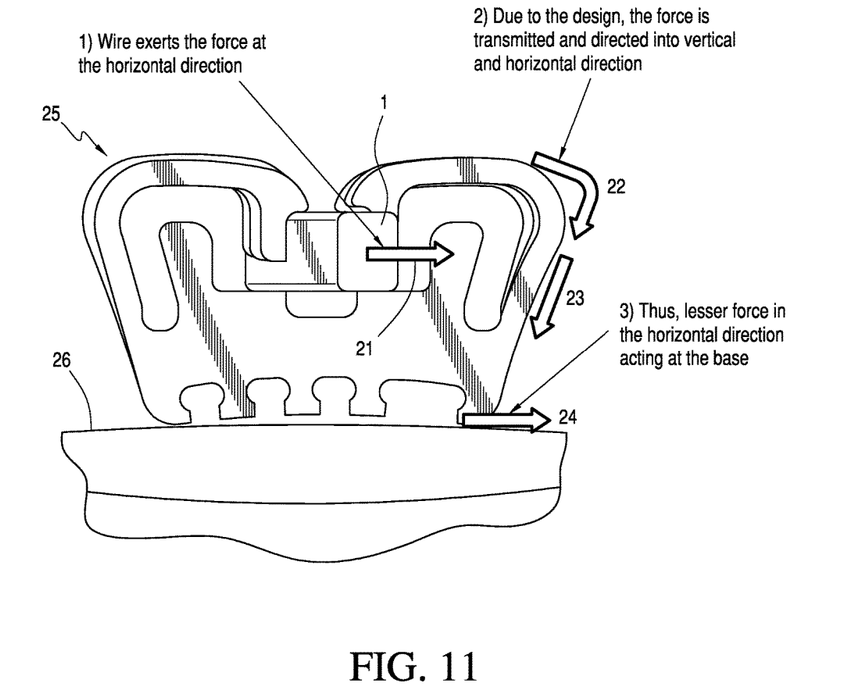
FIG. 11 illustrates an instance of the direction of the various forces exerted through one way of positioning of the archwire and the flexing of the walls of the device.

The present invention thus enables the increasing of tension in the archwire without all of the force being directly imparted to the teeth at once. FIG. 11 illustrates a front elevation view showing how the absorption by the flexing walls of the force also means a lesser force along the base of the device. The direct force (the direction of which is shown by the arrow marked 21) exerted by the archwire (2) on the bracket is diffused due to the flexing of the wall against which the archwire pushes. This results in several other lesser forces indicated by the arrows marked 22, 23 and 24. The resulting lesser force (24) along the base of the device reduces the risk of the device being detached from the tooth (26) itself. The invention also enables easy insertion and removal of archwires. Its design incorporating the hollow walls and separate sets of walls (made of the same or different materials with differing degrees of flexibility) allows the creation of different series of brackets to produce graduated and different intensity of forces for optimum effect on re-positioning of the teeth. The space (12) between the end of the wall (13) and the middle segment (11) of the bracket can also be varied to create different flexibility and absorptive capacities.

The present invention may be embodied in several forms without any deviation from the spirit of the essential characteristics of the invention. The invention should not be limited to the above described embodiments but should be broadly constructed within the scope and spirit of the invention as defined in the appended claims. Various modifications and equivalent arrangements are intended to be included within the scope and spirit of the invention and appended claims. Specific embodiments are to be understood as illustrating the many ways in which the principles of the present invention may be carried out or implemented.

What is claimed is:

1. An orthodontic device for repositioning a tooth, said orthodontic device comprising:
    a base having an upper surface, a lower surface, and a longitudinal axis;
    occlusal walls extending upwardly from a first side of the base and angularly back towards the longitudinal axis;
    gingival walls extending upwardly from an opposing side of the base and angularly back towards the longitudinal axis;
    wherein the upper surface of the base extends from a position where the occlusal walls extend upwardly from the first side of the base, to a position where the gingival walls extend upwardly from the opposing side of the base;
    an archwire-receiving opening defined by opposing ends of the gingival walls and the occlusal walls, and running parallel to the longitudinal axis;

an archwire slot defined by a portion of the upper surface of the base and the opposing ends of the gingival walls and the occlusal walls, and running parallel to the longitudinal axis;

a gingival wall gap defined by two adjacent gingival walls;

an occlusal wall gap defined by two adjacent occlusal walls;

a hollow space defined by the upper surface of the base and an inner surface of each of the occlusal walls, and extending from the first side of the base to the longitudinal axis;

a hollow space defined by the upper surface of the base and an inner surface of each of the gingival walls, and extending from the opposing side of the base to the longitudinal axis;

wherein, for each one of the gingival walls, a gap is defined by the upper surface of the base and an end of the gingival wall;

wherein, for each one of the occlusal walls, a gap is defined by the upper surface of the base and an end of the occlusal wall;

wherein the occlusal walls and the gingival walls are flexible with respect to the base.

2. The orthodontic device as claimed in claim 1, wherein the gingival walls and the occlusal walls have a shape that may be the same or different.

3. The orthodontic device as claimed in claim 1, wherein the flexibility of the occlusal walls and gingival walls is the same or different.

4. The orthodontic device as claimed in claim 1, wherein the orthodontic device is an orthodontic bracket.

5. The orthodontic device according to claim 1, comprising two occlusal walls and two gingival walls.

6. The orthodontic device according to claim 1, comprising three occlusal walls and three gingival walls.

7. The orthodontic device according to claim 1, wherein the occlusal walls and the gingival walls have a thickness that makes the orthodontic device flexible when corrective forces are applied for repositioning the tooth.

8. The orthodontic device according to claim 1, wherein the occlusal walls and the gingival walls have a shape such that, when an archwire inserted in the orthodontic device exerts a force in a direction parallel to a surface of the tooth, the occlusal walls and the gingival walls direct the force into a direction perpendicular to the surface of the tooth, thereby lessening the force in the direction parallel to the surface of the tooth.

9. The orthodontic device according to claim 1, wherein the hollow spaces defined by the occlusal walls and the gingival walls, the gingival wall gap, and the occlusal wall gap are configured so that an archwire inserted into the orthodontic device may push against any point of any one or more walls of the orthodontic device with varying degrees of strength, thereby generating a precisely angled force.

10. The orthodontic device according to claim 1, wherein the archwire slot is defined by walls extending from the upper surface of the base.

11. The orthodontic device as claimed in claim 1, wherein the gap defined by the upper surface of the base and an end of the gingival wall may be the same or different in any two of the gingival walls.

12. The orthodontic device as claimed in claim 1, wherein the gap defined by the upper surface of the base and an end of the occlusal wall may be the same or different in any two of the occlusal walls.

13. The orthodontic device as claimed in claim 1, wherein the gingival wall gap may be the same or different in any two of the gingival walls.

14. The orthodontic device as claimed in claim 1, wherein the occlusal wall gap may be the same or different in any two of the occlusal walls.

15. The orthodontic device as claimed in claim 1, wherein the gap defined by the upper surface of the base and the end of the occlusal wall may be the same or different in any two of the occlusal walls.

16. The orthodontic device as claimed in claim 1, wherein the gap defined by the upper surface of the base and the end of the gingival wall may be the same or different in any two of the gingival walls.

17. A method of repositioning a tooth using the orthodontic device of claim 1, the method comprising:
    affixing the base of the device to the tooth surface;
    moving the archwire past the receiving opening into the slot or cavity; and
    twisting and positioning the archwire within the slot or cavity to exert sufficient corrective force to the tooth to result in repositioning of the tooth.

18. The method as claimed in claim 17, comprising the further step of positioning the archwire to push against the whole or any point or points on any one or more walls of the device.

19. The method as claimed in claim 17, comprising the further step of positioning the archwire to push against the whole or any point or points on any one or more walls of the device with the effect that the wall or walls flex or move to varying degrees depending on the extent of the force exerted by the archwire.

20. The method as claimed in claim 17, comprising positioning of the archwire to create different corrective forces in desired directions.

* * * * *